United States Patent [19]
Ser et al.

[11] Patent Number: 5,437,859
[45] Date of Patent: Aug. 1, 1995

[54] PROCESS FOR THE PREPARATION OF A SOLID DISPERSION OF AT LEAST ONE POLYHYDRIC ALCOHOL IN A FATTY BODY AND THE RESULTING DISPERSION FOR COSMETIC AND PHARMACEUTICAL USE

[75] Inventors: Jean-Claude Ser, Chevilly-Larue; Dolores Miguel, Aubervilliers, both of France

[73] Assignee: L'Oreal, Paris, France

[21] Appl. No.: 917,897

[22] Filed: Jul. 24, 1992

[30] Foreign Application Priority Data

Jul. 26, 1991 [FR] France ................... 9109514

[51] Int. Cl.⁶ .................. A61K 7/42; A61K 7/44; A61K 7/48
[52] U.S. Cl. .................. 424/59; 106/270; 252/352; 514/784; 514/785; 514/787; 514/943
[58] Field of Search ................. 514/943; 424/DIG. 5, 424/63, 64

[56] References Cited

U.S. PATENT DOCUMENTS

| | | | |
|---|---|---|---|
| 4,879,274 | 11/1989 | Kamiya et al. | 514/356 |
| 4,894,222 | 1/1990 | Matravers | 424/59 |
| 5,232,689 | 8/1993 | Katsoulis et al. | 424/401 |

FOREIGN PATENT DOCUMENTS 2237615 2/1975 France ................... 424/63

OTHER PUBLICATIONS

Derwent Abstracts of Great Britain Pat. No. 2,072,503 (1981).
French Search Report of FR 91 09514 Apr. 10, 1992.
Patent Abstracts of Japan, vol. 13, No. 399 (C-632)(3747), Sep. 1989.
Patent Abstracts of Japan, vol. 8, No. 266 (C-255)(1703, Dec. 1984).
Patent Abstracts of Japan, vol. 15, No. 238 (C-841)(4766), Jun. 1991.

*Primary Examiner*—C. Warren Ivy
*Assistant Examiner*—Evelyn Huang
*Attorney, Agent, or Firm*—Cushman Darby & Cushman

[57] ABSTRACT

A process for preparing a stable and anhydrous solid dispersion, containing from 20 to 95 weight percent of a fatty body, constituted of 10 to 50 weight percent of at least one wax having a melting point greater than 55° C., and from 4 to 50 weight percent of a polyhydric alcohol, involves heating the fatty body and the polyhydric alcohol to a temperature between 65° and 95° C. and mixing the heated components in a turbine rotating at a speed greater than 1500 rpm. The resulting dispersion is employed in the production of cosmetics in stick form.

15 Claims, No Drawings

PROCESS FOR THE PREPARATION OF A SOLID DISPERSION OF AT LEAST ONE POLYHYDRIC ALCOHOL IN A FATTY BODY AND THE RESULTING DISPERSION FOR COSMETIC AND PHARMACEUTICAL USE

The present invention relates to a process for preparing a solid dispersion containing, in the dispersed state, a significant amount of polyhydric alcohol ("polyol") in a fatty body, the resulting dispersion being intended for cosmetic or pharmaceutical use.

Cosmetic or pharmaceutical solid fatty products, conventionally employed principally in the form of sticks, for example, lip sticks, exhibit the disadvantage of not having hydrating characteristics.

To reduce this disadvantage, attempts have been made to incorporate water when preparing these emulsified products.

In this regard mention can be made of French patent application No. 73 26446 (2.237.615) which describes a water-in-oil emulsion containing 1 to 50 percent by weight of water.

However, this type of composition poses water evaporation problems.

The composition described in this patent application also contains from 1 to 10 percent of a polyhydroxylated compound in order to obtain a uniform distribution of the dye substances in the water-in-oil emulsion.

The water evaporation problem of solid dispersions has been resolved, according to European patent application No. EP 374.332, by incorporating a silicone oil as well as an organopolysiloxane modified by a polyoxyalkylene.

The compositions thus modified can also contain small amounts of polyols as additional humectants.

However, no product containing water in any substantial amount has yet to be commercialized at the present time simply because of water loss problems which appear not yet to have been resolved in a satisfactory manner.

According to Japanese patent application publication No. 1-143.812, there is described the incorporation of a significant amount of polyvalent alcohols in a solid emulsion for cosmetic use by the expedient of a silicone oil and modified polyoxyalkylenated organopolysiloxane as an emulsifying agent.

Now, with this system, it is difficult to obtain good homogeneity of the formulation.

One goal of the present invention is to reduce the difficulties described above.

Following various studies, it has been noted, in an unexpected and surprising manner, that a significant amount of polyhydric alcohol can be incorporated in a solid dispersion by the use of, during the incorporation, a turbine rotating at a minimum speed which produces very small size particles.

The present invention relates then to a process for the preparation of a stable andanhydrous solid dispersion comprising from 20 to 95 percent and, preferably, from 40 to 85 percent of a fatty body, constituted by 10 to 50 percent of at least one wax having a melting point greater than 55° C., and from 4 to 50 percent of a dispersed polyhydric alcohol, preferably from 6 to 40 percent, and more particularly from 8 to 25 percent, characterized in that the said fatty body and the polyhydric alcohol are heated to a temperature between 65° and 95° C. and that a turbine operated at a rotation speed of at least 1500 rpm and preferably, between 2500 and 3500 rpm is employed to mix these heated components.

By the expression "solid dispersion" is meant a composition which is solid at a temperature between 0° and 50° C., which temperature corresponds to that of storage temperature and the temperature at which the cosmetic compositions is employed.

The present invention also relates a stable and anhydrous solid dispersion comprising from 20 to 95 percent of a fatty body, constituting the continuous phase, and from 4 to 50 percent, preferably, from 6 to 40 percent and more particularly from 8 to 25 percent, of a dispersed polyhydric alcohol characterized in that the average size of the polyhydric alcohol particles is less than or equal to 1 μm and preferably between 0.01 and 0.8 μm and in that the fatty body is constituted by 10 to 50 percent by weight of at least one wax having a melting point greater than 55° C.

The dispersion according to the present invention provides cosmetic products having excellent emollient properties on application to the skin.

The solid dispersions according to the invention are employed in molded fatty products such as lip rouge, complexion foundations, eye shadow formulations, cheek rouge and principally in products in the form of sticks.

According to one preferred embodiment, the solid dispersion, according to the invention can also contain up to 10 percent of a mineral or organic charge or filler such as talc, starch and the like.

It is also possible that the dispersion, according to the invention, contain up to about 30 percent (preferably from 0.1 to 20 percent ) of a pigment and from 0.01 to 20 percent (preferably from 0.5 to 10 percent) of a hydrocarbon surfactant. The use of a hydrocarbon surfactant provides a finer dispersion and thus a more satisfactory stick.

In accordance with a more particularly preferred embodiment, it is possible to add to the dispersion, according to the invention, a sufficient amount of copolymer for increased stabilization against a moist atmosphere.

Such polymers must be liposoluble and have a low amount of hydrophilic units.

Among these, mention can be made of polyalkylenes (principally polyethylenes and polybutenes), polyacrylates and silicone polymers compatible with fatty bodies.

Among the polyalkylenes mention can be made of polybutene, principally that sold by Amoco under the trade name INDOPOL.

The weight ratio of the polymer to the polyhydric alcohol is generally less than 4 and is,preferably, between 0.25 and 2.

In accordance with the invention, the polyhydric alcohol can be a compound having 2-8 carbon atoms and from 2 to 6 hydroxy functions. Among these compounds mention can be made of ethylene glycol, glycerine, 1,2-propanediol, diglycerine, erythritol, arabitol, adonitol, sorbitol and dulcitol.

The polyhydric alcohol can also be a polyether alcohol having an average molecular weight between 150 and 600 and among these mention can be made of polyethylene glycol 300 and polyglycerine 500.

The polyhydric alcohol can optionally be enriched with hydrosoluble active agents such as amino acids (for example arginine, lysine, proline and serine), vitamins such as D,L Panthenol and sunscreen agents.

These can be present in an amount of from 0.05 to 5 percent.

As indicated above, the fatty body in accordance with the invention is constituted of 10 to 50 weight percent of at least one wax whose melting point is greater that 55° C., the remainder being either a wax having a melting point lower than 55° C. or an oil or a mixture thereof. The final melting point of the entire mixture must be lower than 110° C. which does not preclude the use of certain constituents of the mixture having a higher melting point.

Among waxes having a melting point greater than 55° C., capable of being employed in accordance with the invention, mention can be made of animal, vegetable, mineral and synthetic waxes and various fractions of natural waxes, all these waxes having, as a general rule, a melting point between 55° and 110° C., and a needle penetration value, at 25° C., between about 3 and 40, as measured in accordance with the American standard, ASTM D5 or the French standard, NFT 004. The principle of the needle penetration measurement according to these two standards consists in measuring the depth, expressed in tenths of millimeters, at which penetrates a standardized needle (weighing 2.5 g, placed in a needle holder weighing 47.5 g, or a total of 50 g), placed on the wax for 5 minutes.

Among the animal waxes that can be employed, mention can be made, among others, of beeswax, lanolin wax, china insect wax and lanolin derivatives. Representative vegetable waxes include, among others, Carnauba wax, Candelilla wax, Ouricurry wax, cork fiber wax, sugar cane wax and Japan wax. Representative mineral waxes, include, in particular, paraffins, microcrystalline waxes, lignite waxes (Montan wax) and ozokerites. Representative synthetic waxes include, in particular, polyethylene waxes, waxes obtained by Fischer-Tropsch synthesis, and waxy polymers as well as their esters. All these waxes are well known to those skilled in the art.

Among the waxes having a melting point lower than 55° C. mention can be made of mineral waxes, such as petrolatum; hydrogenated oils solid at 25° C., such as hydrogenated ricin oil, hydrogenated palm oil, hydrogenated tallow and hydrogenated coconut oil; fatty esters solid at 25° C., such as propylene glycol myristate and myristyl myristate, mono-, di- and triglycerides solid at 25° C., rosin and its derivatives, cetyl alcohol, calcium, magnesium, zinc and aluminum oleates, myristates, lanolates, stearates and dihydroxy stearates.

Representative oils, capable of being employed in admixture with the waxes, include, particularly, mineral oils such as paraffin oil, petrolatum oil and mineral oils having a boiling point between 310° and 410° C.;

oils of animal origin, such as perhydrosqualene;

vegetable oils such as sweet almond oil, calophyllum oil, palm oil, avocado oil, jojoba oil, olive oil, ricin oil and cereal germ oils such as wheat germ oil;

silicone oils, such as dimethylpolysiloxane;

perfluorinated oils such as the "FOMBLINS" sold by Montefluos;

synthetic esters such as Purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and di-isopropyl adipate;

organic alcohols such as oleic alcohol, linoleic alcohol, linolenic alcohol, isostearyl alcohol and octyl dodecanol and esters derived from lanolic acid such as isopropyl lanolate and isocetyl lanolate, Among the oils mention can also be made of the acetylglycerides, octanoates and decanoates of alcohols and polyalcohols, such as those of glycol and glycerol, the ricinoleates of alcohols and poly alcohols, such as that of cetyl.

The fatty bodies can optionally contain pigments.

As colored pigments, mention can be made of carbon black or black iron oxide, chromium oxides, yellow and red iron oxides, the ultramarines (aluminosilicate polysulfides), manganese pyrophosphate, ferric blue, titanium dioxide and finally certain metallic powders such as those of silver and aluminum. The pigments are most often employed in admixture with nacreous agents such as bismuth oxychloride, mica-titanium, guanine crystals and certain organic dyes, such as cochineal carmine and organic lakes.

These lakes which currently are employed to impart to the lips and skin a make-up effect, are salts of calcium, barium, aluminum and zirconium, acid dyes such as halogen acid dyes, azo dyes, anthraquinone dyes and the like.

Among these lakes, mention can be made, in particular, of those known under the names of D and C Red 21, D and C orange 5, D and C Red 27, D and C Orange 10, D and C Red 3, D and C Red 7, D and C Red 2, D and C Red 4, D and C Red 8, D and C Red 33, D and C Yellow 5, D and C Yellow 6, D and C Green 5, D and C Yellow 10, D and C Green 3, D and C Blue 1, D and C Blue 2, D and C Violet 1 and the like.

When the dispersions are provided in the form of makeup products they can also contain antioxidant agents in an amount of 0 to 3%, preferably, 0.05 to 0.5%, such as propyl, octyl and dodecyl esters of gallic acid, butylhydroxytoluene, butylhydroxyanisole, as well as perfumes, preservatives such as methyl or propyl parahydroxybenzoate. These additives are present, in accordance with their solubility, either in the fatty phase or in the polyhydric alcohol dispersed phase.

The fatty body can carry one or several liposoluble active ingredients commonly employed in cosmetic or pharmaceutical products in an amount ranging from 0.05 to 5 percent and preferably from 0.5 to 3 percent. Among these mention can be made of vitamin derivatives, such as tocopherol acetate and vitamin A palmitate, essential fatty acids, sphingocerils and soluble sunscreen agents.

Representative surfactants, conventionally employed in lip rouges, include anionic or nonionic surfactants, having an HLB lower than 10 (preferably lower than 5) with the exception of silicone surfactants. Representative nonionic surfactants include the lecithins, succinyl glycerides and alkylphosphates.

Representative anionic surfactants include magnesium lanolate, zinc lanolate, copper lanolate, arginine lanolate and magnesium octadecanoate.

Generally, the process according to the invention comprises the following steps:

The fatty phase constituted of 10 to 50 percent of at least one wax having a melting point greater than 55° C., and containing optionally in dispersion pigments and/or charges, is heated to a temperature greater than the highest melting point of the waxes (finishing temperature) and, on the other hand, the polyhydric alcohol, optionally containing soluble additives, is heated to the same temperature. The two heated components are mixed using a turbine operated at a rotation speed between 1500 and 3500 rpm and preferably between 2500 and 3500 rpm so as to produce the dispersion which is then molded in an appropriate mold.

The turbine employed in the process of the invention can be any commercial model for the preparation of cosmetic or pharmaceutical compositions. For example the turbine can be a Moritz turbine.

In order to determine the size of the dispersed particles, according to the invention, any appropriate technique, such as cryofracture or optic microscopy can be used.

The following non-limiting examples illustrate the invention:

EXAMPLE 1

In accordance with the invention a solid dispersion in the form of a lipstick having the following composition is prepared.

|  | Weight percent |
| --- | --- |
| Ricin oil | 3 |
| Petrolatum oil | 9 |
| Lanolin | 15 |
| Butylhydroxytoluene (BHT) | 0.2 |
| Beeswax | 8.8 |
| Ozokerite | 10 |
| Soy lecithin | 4 |
| Glycerine | 10 |
| Polyethylene glycol 300 | 12 |
| Talc | 3 |
| D&C Red 27 | 5 |
| Black iron oxide | 2 |
| D&C Red 7 | 6 |
| Polybutene (INDOPOL, sold by Amoco) | 12 |
| Perfume, sufficient amount | |

The lipstick is prepared in the following manner:

The fatty phase constituted of the ricin oil, petrolatum oil, lanolin, butylhydroxytoluene (BHT), beeswax, ozokerite, soy lecithin and polybutene is heated; the dyes are ground in the fatty phase and then the talc is added. Moreover, the mixture constituted of the glycerine and polyethylene glycol 300, to which one adds the perfume is heated; a Moritz turbine operated at a rotation speed of 3000 rpm is employed to mix the fatty phase and the alcohol phase until a composition having a consistency suitable for molding, all while cooling, is obtained.

The average size of the dispersed particles is between 0.03 and 0.5 μm.

EXAMPLE 2

In accordance with the invention a solid dispersion in the form of a stick having the following composition is prepared.

|  | Wt percent |
| --- | --- |
| Ricin oil | 20 |
| Jojoba oil | 20 |
| Isopropyl lanolate | 27.9 |
| BHT | 0.1 |
| Microcristalline wax | 8 |
| Carnauba wax | 8 |
| Trioleyl phosphate (HOSTAPHAT KO 3000, sold by Hoeschst) | 1 |
| Glycerine | 15 |
| Pigment, sufficient amount | |

The stick is prepared as in Example 1.

The average size of the particles is between 0.03 and 0.5 μm.

EXAMPLE 3

In accordance with the invention a solid dispersion in the form of a stick having the following composition is prepared.

|  | Wt percent |
| --- | --- |
| Ricin oil | 17 |
| Jojoba oil | 17 |
| Isopropyl lanolate | 23.9 |
| BHT | 0.1 |
| Microcrystalline wax | 4 |
| Carnauba wax | 4 |
| Trioleyl phosphate (HOSTAPHAT KO 300, sold by Hoechst) | 1 |
| Glycerine | 15 |
| Vinyl polylaurate | 10 |
| Polyethylene | 8 |
| Pigments, sufficient amount | |

The stick is prepared as in Example 1.

The average size of the particles is between 0.03 and 0.5 μm.

EXAMPLE 4

In accordance with the invention a solid dispersion, molded as an eye shadow and having the following composition, is prepared.

|  | Wt percent |
| --- | --- |
| Petrolatum oil | 30.65 |
| Petrolatum | 10 |
| Carnauba wax | 5 |
| Ethylene and acrylic derivatives copolymer | 5 |
| Mica-titanium | 5 |
| Titanium oxide | 5 |
| Talc | 5 |
| D&C Red 7 | 0.2 |
| Brown iron oxide | 2 |
| Polybutene | 10 |
| BHT | 0.05 |
| Propyl parahydroxybenzoate | 0.1 |
| Glycerine | 20 |
| Lecithin | 2 |

The stick is prepared as in Example 1.

The average size of the particles is between 0.03 and 0.5 μm.

EXAMPLE 5

In accordance with the invention a solid dispersion, molded as a complexion foundation, having the following composition is prepared.

|  | Wt percent |
| --- | --- |
| Microcyrstalline wax | 8 |
| Carnauba wax | 4 |
| Octyl palmitate | 14.5 |
| Isoparaffin | 23 |
| Isopropyl lanolate | 4 |
| Propyl parahydroxybenzoate | 0.2 |
| Yellow iron oxide | 1 |
| Brown iron oxide | 0.37 |
| Black iron oxide | 0.15 |
| Titanium oxide | 5.47 |
| Zinc oxide | 3 |
| Talc | 3 |
| Nylon powder | 3 |
| Microspheres, sold under the | 1.2 |

-continued

|  | Wt percent |
|---|---|
| commercial name "EXPANCEL DE" by Kemanord Plast AB | |
| Dimethicone | 0.3 |
| Vinyl polylaurate | 12.5 |
| Glycerine | 15 |
| Magnesium lanolate | 1 |
| Perfume | 0.31 |

The molded complexion foundation is prepared as in Example 1.

The average size of the particles is between 0.03 and 0.5 μm.

EXAMPLE 6

According to the invention a solid dispersion, molded as a complexion foundation, having the following composition is prepared.

|  | Wt. percent |
|---|---|
| Triglycerides of caprylic and capric acids, (MIGLYOL 810, sold by Huls) | 3 |
| Sesame oil | 10 |
| Acetylated lanolin | 8 |
| Candelilla wax | 8 |
| Microcyrstalline wax | 12 |
| Magnesium lanolate | 5 |
| Polyglycerine 500 | 20 |
| FD&C Yellow 6 | 5 |
| D&C Red 7 | 5 |
| Titanium dioxide | 2 |
| Vinyl polylaurate | 15 |
| Polystearylmethylsiloxane (ABIL WAX 9000, sold by Goldschmidt) | 5 |
| Butylhydroxytoluene (BHT) | 0.2 |
| Perfume, sufficient amount | |

The complexion foundation is prepared as in Example 1.

The average size of the particles is between 0.03 and 0.5 μm.

We claim:

1. A stable and anhydrous solid cosmetic dispersion which provides emollient properties on application to the skin comprising from 20 to 95 weight percent of a fatty body and 4 to 50 weight percent of particles of a polyhydric alcohol having from 2 to 8 carbon atoms and 2 to 6 hydroxyl groups, wherein the average size of said polyhydric alcohol particles dispersed therein is lower than or equal to 1 μm and said fatty body comprises from 10 to 50 weight percent of at least one wax having a melting point greater than 55° C.

2. The dispersion of claim 1 wherein said polyhydric alcohol is selected from the group consisting of ethylene glycol, glycerin, 1,2-propanediol, diglycerine, erythritol, arabitol, adonitol, sorbitol, dulcitol and mixtures thereof.

3. The dispersion of claim 1 wherein said fatty body is present in an amount ranging from 40 to 85 weight percent and said polyhydric alcohol is present in an amount ranging from 6 to 40 weight percent.

4. The dispersion of claim 1 wherein said polyhydric alcohol is a polyether alcohol having an average molecular weight ranging from 150 to 600.

5. The dispersion of claim 4 wherein said polyether alcohol is selected from the group consisting of polyethylene glycol 300, polyglycerine 500 and mixtures thereof.

6. The dispersion of claim 1 which includes a hydrocarbon surfactant present in an amount ranging from 0.01 to 20 weight percent.

7. The dispersion of claim 1 which includes a hydrocarbon surfactant present in an amount ranging from 0.5 to 10 weight percent.

8. The dispersion of claim 1 wherein said particles of polyhydric alcohol contain a hydrosoluble active material in an amount ranging from 0.05 to 5 weight percent based on the total weight of said dispersion, said active material being selected from the group consisting of an amino acid, a vitamin and a sunscreen agent.

9. The dispersion of claim 1 which also contains at least one polymer capable of stabilizing said dispersion in a moist atmosphere.

10. The dispersion of claim 9 wherein said polyhydric alcohol is present in an amount such that the weight ratio of said polymer to polyhydric alcohol is less than 4.

11. The dispersion of claim 9 wherein said polyhydric alcohol is present in an amount such that the weight ratio of said polymer to polyhydric alcohol is between 0.25 and 2.

12. The dispersion of claim 9 wherein said polymer is selected from a polyalkylene, a polyacrylate and a silicone polymer.

13. The dispersion of claim 1 which also contains up to 30 weight percent of a pigment.

14. The dispersion of claim 1 which also contains from 0.1 to 20 weight percent of a pigment.

15. The dispersion of claim 1 which also contains up to 10 weight percent of a mineral or organic charge selected from the group consisting of talc and starch.

* * * * *